United States Patent [19]

Crause et al.

[11] Patent Number: 5,180,668
[45] Date of Patent: Jan. 19, 1993

[54] HIRUDIN DERIVATIVE

[75] Inventors: Peter Crause, Offenbach; Paul Habermann, Frankfurt am Main; Dominique Tripier, Eppstein/Taunus, all of Fed. Rep. of Germany

[73] Assignee: Hoechst Aktiengesellschaft, Frankfurt am Main, Fed. Rep. of Germany

[21] Appl. No.: 295,422

[22] Filed: Jan. 10, 1989

[30] Foreign Application Priority Data

Feb. 23, 1988 [DE] Fed. Rep. of Germany ....... 3805540

[51] Int. Cl.⁵ .................... A61K 37/64; C07K 13/00; C07H 21/04; G12N 15/64
[52] U.S. Cl. .................................. 435/69.2; 530/324; 530/855; 514/12; 435/69.1; 435/69.6; 435/320.1; 536/23.5
[58] Field of Search .................. 530/324, 855; 514/12; 435/69.1, 69.2, 69.6, 320.1; 536/27

[56] References Cited

U.S. PATENT DOCUMENTS 4,767,742  8/1988  Dodt et al. ................... 530/324

FOREIGN PATENT DOCUMENTS

WO8603517  6/1986  PCT Int'l Appl. .

OTHER PUBLICATIONS

Harvey et al, (1986) Proc. Natl. Acad. Sci. 83, 1084–1088.
Creighton, T. E. (1984) "Proteins: Structure and Molecular Properties," W. H. Freeman and Co., New York, pp. 1–24.

Primary Examiner—Robert A. Wax
Assistant Examiner—R. Keith Baker
Attorney, Agent, or Firm—Finnegan, Henderson, Farabow, Garrett and Dunner

[57] ABSTRACT

A hirudin derivative which has the N-terminal amino acid sequence Leu-Thr-Tyr-Thr-Asp shows high biological activity. Moreover, this hirudin derivative can be obtained very efficiently by genetic engineering preparation in yeasts.

6 Claims, 2 Drawing Sheets

HIRUDIN DERIVATIVE

Derivatives of hirudin and the genetic engineering preparation thereof are disclosed in the European Patent Application with the publication number (EP-A) 0,171,024.

It has now been found that the hirudin derivative of the amino acid sequence

```
 0   1                                          10
Leu—Thr—Tyr—Thr—Asp—Cys—Thr—Glu—Ser—Gly—Gln—Asn—Leu—Cys—

20
Leu—Cys—Glu—Gly—Ser—Asn—Val—Cys—Gly—Gln—Gly—Asn—Lys—Cys—

30                                      40
Ile—Leu—Gly—Ser—Asp—Gly—Glu—Lys—Asn—Gln—Cys—Val—Thr—Gly—

50
Glu—Gly—Thr—Pro—Lys—Pro—Gln—Ser—His—Asn—Asp—Gly—Asp—Phe—

60
Glu—Glu—Ile—Pro—Glu—Glu—Tyr—Leu—Gln
``` has a number of advantages. The numbering used in EP-A 0,171,024 has been retained in this sequence. Hirudin and its derivatives differ in biological activity, which can be attributed to differences in the affinity for thrombin and/or differences in the stability. The hirudin derivative according to the invention is, surprisingly, distinguished by special activity.

It has also been found that the hirudin derivative according to the invention is particularly advantageously expressed in yeasts. Comparison experiments showed that analogous hirudin derivatives starting with N-terminal Thr-Tyr or Ile-Tyr are expressed only in low yields.

Expression from yeast cells is advantageous not only because the hirudin derivative is secreted but also, and especially, because it is virtually quantitavely in the correctly folded form and has high activity.

Figure 1:
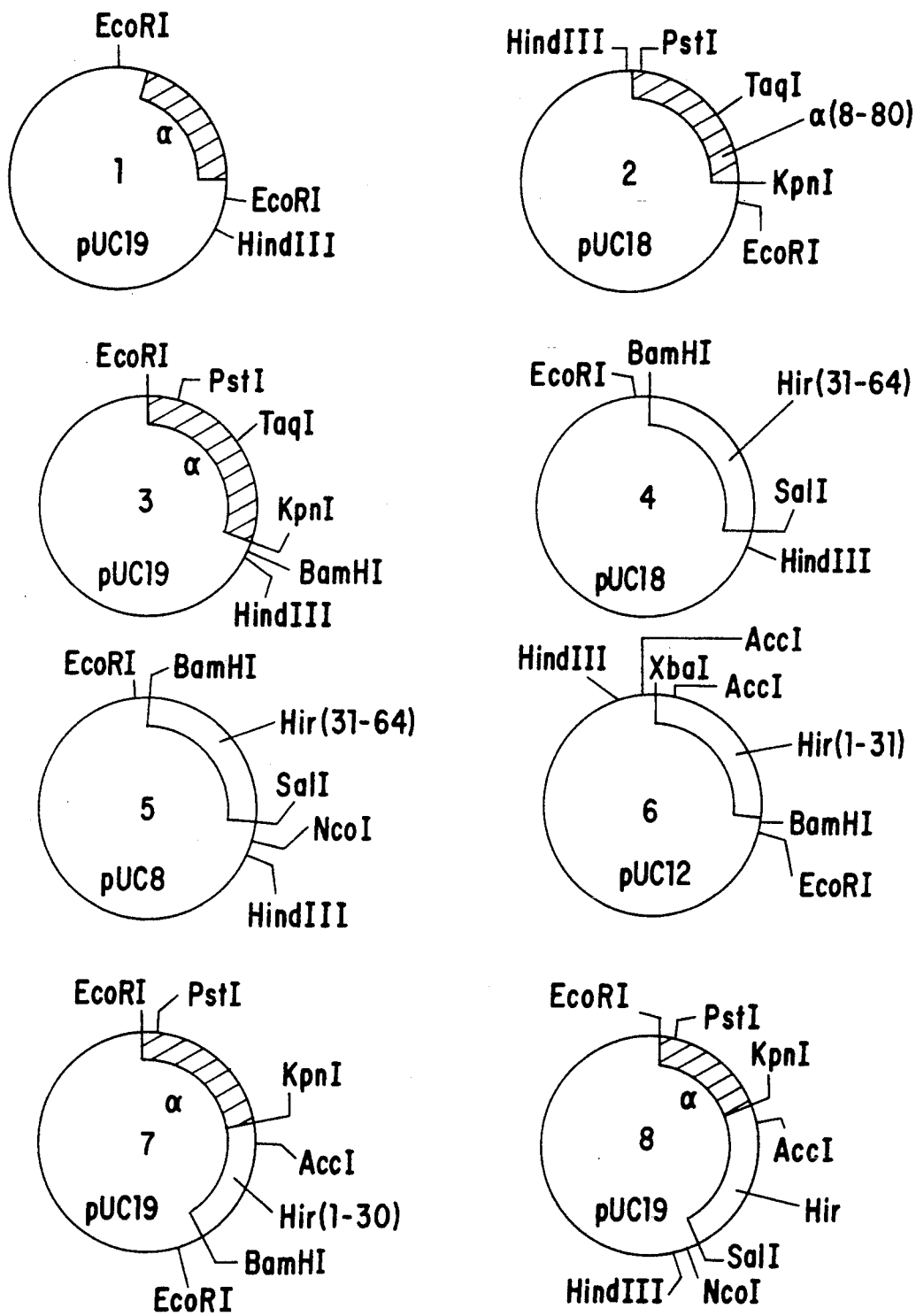
FIG. 1 shows cloning vectors useful for making a gene structure which codes for the yeast MFα precursor protein and the hirudin derivative according to this invention.

The hirudin derivative according to the invention can, of course, also be prepared by different methods, for example by expression in bacteria or in higher eukaryotic cells such as insect cells or animal cells. However, expression from yeast systems is preferred, for example using the yeast species listed in EP-A 0,248,227, for example, *Pichia pastoris, Hansenula polymorphis, Schizosaccharomyces pombe* or, preferably, *Saccharomyces cerevisiae.*

A large number of vectors are known for expression in yeasts, e.g. from EP-A 0,060,057, 0,008,632, 0,116,201, 0,121,884, 0,123,544 and 0,195,691. The preparation of the hirudin derivative according to the invention is described hereinafter using the yeast α factor system, but this is to be understood to be merely by way of example, since other expression systems can also be used in a manner known per se.

The structure of the yeast pheromone gene MFα is known from Kurjan and Herskovitz, Cell 30 (1982) 933-943, where the possibility of expression of other genes and the secretion of the gene products is also discussed. In this connection, reference may also be made to Brake et al., Proc. Natl. Acad. Sci 81 (1984), 4642-4646.

The yeast vectors which are advantageously used are so-called shuttle vectors which have an origin of replication of a bacterial plasmid and of a yeast plasmid, as well as genes for selection in both host systems. Furthermore, vectors of this type contain the promoter sequences necessary for the expression of foreign genes and, where appropriate, a terminator sequence for improving the yield, so that the heterologous gene—expediently fused to secretory signals—is located between the promoter and terminator.

The invention is explained in detail by the Examples which follow. Percentage data relate to weight.

EXAMPLE 1: Construction of the expression vector

Firstly the DNA sequence I (Table 1) is synthesized by the phosphite method. This DNA sequence codes for amino acids 49 to 80 of the MFα precursor protein and essentially corresponds to the natural DNA sequence.

DNA sequence I is initially used as a probe for isolating the gene for the α factor, and for this purpose is labeled with $^{32}P$. This probe is used to isolate the gene from a genomic λgt11 yeast gene bank (as are now commercially available from, for example, Clontech Laboratories Inc., 4055 Fabian Way, Palo Alto, CA94303). For this purpose, λgt11 phages which carry the α factor gene are identified in a plaque-hybridization experiment. Phages from plaques identified as positive are isolated and propagated, and the DNA is obtained. The latter is cleaved with EcoRI and analyzed on a 0.8% agarose gel. After a Southern transfer experiment, the membrane is hydridized with the $^{32}P$-labeled DNA sequence I. Phage DNA which has an approximately 1.75 kb fragment which hybridizes with DNA sequence I is again cleaved with the enzyme, and the corresponding fragment is isolated. The vector pUC 19 is opened with EcoRI and reacted with the 1.75 kb fragment using T4 ligase. The cloning vector 1 is obtained.

The cloning vectors which are listed in Table 2 were all constructed on the basis of a pUC plasmid. This table shows only the polylinker region of these vectors in the usual 5'-3' direction, with the MFα sequences being indicated by dotted lines, and the hirudin sequences being indicated by broken lines. Full lines denote pUC and linker sequences. FIG. 1 shows these cloning vectors as diagrams (not drawn to scale).

The strain *E. coli* 79/02 is transformed with the ligation mixture. White colonies are isolated, the plasmid DNA is obtained from them, and plasmids which contain the 1.75 kb EcoRI fragment are identified.

The natural DNA sequence of the precursor protein for MFα contains in the region of the codons for amino acids 8 to 10 a PstI cleavage site and in the region of the codons for amino acids 48/49 a TaqI cleavage site. The fragment which codes for amino acids 9 to 48 of the MFα precursor sequence is now isolated from the isolated plasmid DNA by reaction with PstI and TaqI. The vector pUC18 is opened with PstI and KpnI and is reacted with the PstI-TaqI fragment as well as with the synthetic DNA sequence I using T4 ligase. E. coli 79/02 is transformed with the ligation mixture. The transformation mixture is plated out on IPTG-Xgal-Ap plates. White colonies are isolated, and the plasmid DNA of these clones is characterized by restriction analysis. In this way is obtained the cloning vector 2 which codes for amino acids 8 to 80 of the MFα precursor sequence.

The said coding sequence is cut out of the cloning vector 2 by reaction with PstI and KpnI, and is introduced into the ligation described below. For this purpose, the cloning vector 1 is reacted with EcoRI and partially with PstI, and the fragment comprising the coding sequence for the first 8 amino acids of the MFα precursor sequence is isolated. In addition, the vector pUC19 is opened with EcoRI and KpnI and ligated with the two fragments described, resulting in the cloning vector 3. The latter codes for the complete MFα precursor sequence up to amino acid 80.

The starting material used for most of the hirudin sequence is the synthetic gene which is depicted in EP-A 0,171,024 as "DNA sequence I" and is shown in the present Table 1 as DNA sequence IV. The restriction enzyme cleavage sites in this sequence are emphasized by underlining: AccI cuts in the region of amino acids 1 to 3, BamHI cuts in the region of amino acids 30/31, and SacI cuts starting with the last stop codon. The protruding sequence for XbaI is located at the 5' end of the gene, and the protruding sequence for SalI is located at the 3' end.

Figure 2A:
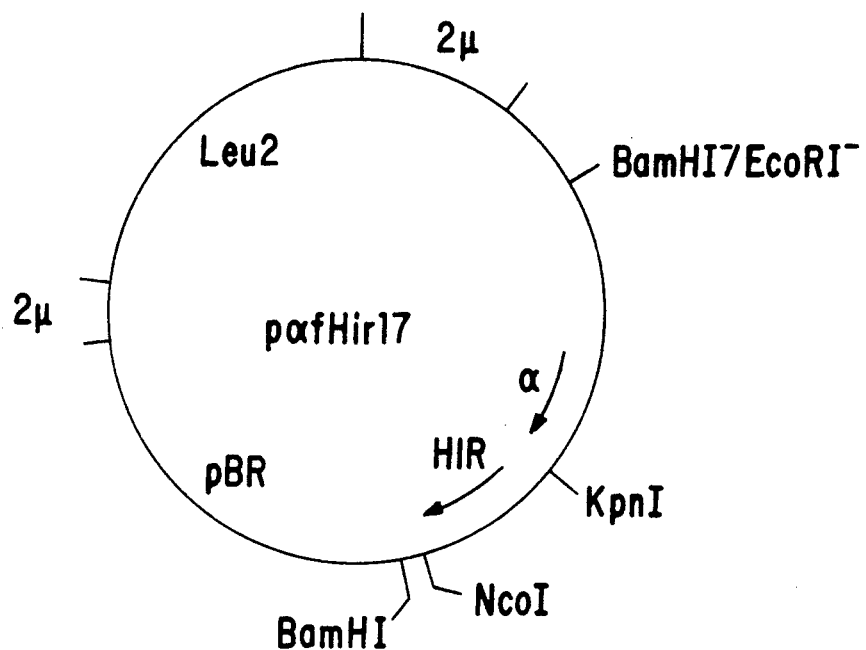
FIGS. 2A and 2B show a yeast expression vector containing this gene structure.
Figure 2B:
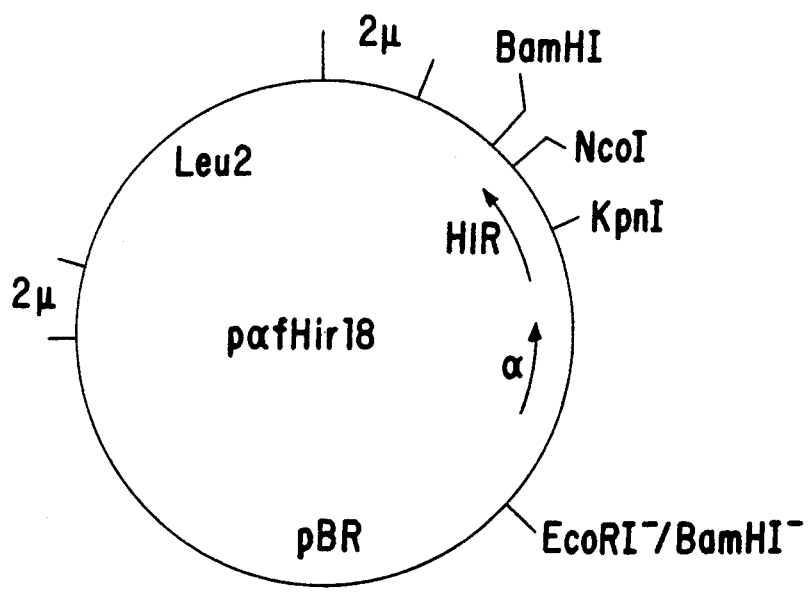

This synthetic gene was subcloned in two parts (FIGS. 1 and 2 in EP-A 0,171,024). These subcloning vectors are depicted in Table 2 under No. 4 (corresponding to FIG. 2 of EP-A 0,171,024) and 6 (corresponding to FIG. 1 of EP-A 0,171,024).

The cloning vector 4 is opened with HincII and HindIII, and the linearized DNA is ligated with DNA sequence II (Table 1). An NcoI cleavage site has been formed at the site which has undergone blunt-ended ligation in the cloning vector 5 obtained in this way.

The fragment coding for the hirudin part-sequence is cut out of the cloning vector 6 by total digestion with BamHI and AccI. This fragment is then ligated with the cloning vector 3 which has been opened with BamHI and KpnI, and with DNA sequence III (Table 1). The last three codons in DNA sequence III are numbered in the same way as in DNA sequence IV (Table 1). This results in the cloning vector 7 which codes for the first 80 amino acids of the MFα precursor sequence and the first 30 amino acids of the hirudin derivative according to the invention, as has been confirmed by DNA sequence analysis.

The fragment which codes for amino acids 31 to 64 of hirudin is cut out of the cloning vector 5 with BamHI and HindIII. This fragment is ligated into the cloning vector 7 which has been opened with the same enzymes, resulting in the cloning vector 8 which codes for the first 80 amino acids of the MFα precursor sequence and the complete sequence of the hirudin derivative according to the invention. The structure of this plasmid is confirmed by restriction analysis.

The plasmid Yep13 (Broach, et al., Gene 8 (1979) 121) is opened with BamHI, and the protruding ends are filled in with Klenow polymerase. The DNA is precipitated with ethanol and treated with bovine alkaline phosphatase.

The fragment coding for the hirudin derivative and the MFα precursor sequence is cut out of the cloning vector 8 (Table 2) with NcoI and EcoRI, and the protruding ends are filled in as described.

The two blunt-ended DNA sequences are ligated together, resulting in plasmids pαfHir17 and pαfHir18 (FIG. 2). These two plasmids differ only in the orientation of the inserted fragments.

It is possible to insert, as described in EP-A 0,171,024, a terminator downstream of the inserted sequence (FIGS. 4 to 6 of EP-A 0,171,024). Suitable for this purpose are the NcoI and/or BamHI cleavage sites.

After amplification of the plasmid DNA in E. coli MM294, the plasmid pαfHir17 is transformed into the leucine-dependent yeast strains Y79 (α, trp1-1, leu2-1) (Cantrell et al., Proc. Acad. Natl. Sci. USA 82 (1985) 6250) and DM6-6 (60 /αleu2-3,112::ura3+/leu2::lys2+, trp1−/trp1−, his3-11, 15/his3-11, 15, ura$^3$−/ura3−, lys2−/lys2−, $^{arg}$4-17/arg4+, ade1−/ade1+) (Maya Hanna, Dept. Mol. Biol. Massachusetts General Hospital, Boston, USA) by the lithium method of Ito, H. et al., J. Bacteriol. 153 (1983) 163. Isolation of single colonies which are able to grow on selective medium without added leucine is carried out. Yeast minimal medium is inoculated with the individual colonies and incubated at 28° C. for 24 hours. The cells are spun down and the supernatant is examined in a thrombin inhibition assay for hirudin activity. The plasmid DNA from yeast clones whose supernatant shows hirudin activity is reisolated and characterized by restriction analysis. The transformed yeast strains are used for the expression tests which follow.

EXAMPLE 2: EXPRESSION 10 ml of yeast complete medium is inoculated with cells taken from a fresh overnight culture of a strain obtained as in Example 1, from selective medium in such a way that an optical density $OD_{600}=0.1$ is reached. The culture is shaken at 28° C. for 8 hours and then 90 ml of fresh medium was added. The culture is then shaken for a further 20 hours. The cells are spun down, and the hirudin activity in the supernatant is determined.

EXAMPLE 3: WORKING UP

Supernatant obtained as in Example 2 is acidified to pH 3 to 5 and applied to an adsorption column containing a porous adsorber resin composed of a copolymer of stryene and divinylbenzene (®DIAION HP 20) which has been equilibrated with 0.1M acetic acid. Washing with Tris.HCl (pH 8.5) and 50 mM acetic acid is followed by elution with 30% strength isopropanol. The fractions containing the hirudin derivative are combined and purified on a Q-SEPHAROSE® column which has been equilibrated with 20 mM piperazine.HCl (pH 6). Elution in this case is with a 0-0.25M NaCl gradient. The fractions containing the hirudin derivative are again combined and purified by HPLC on a C18 reversed phase chromatography column. The pure product obtained in this way is then subjected to automated protein sequence analysis.

EXAMPLE 4: COMPARISON EXAMPLE

If the procedure of Example 1 is used but with the following sequences in place of DNA sequence III (Table 1), the only minimal hirudin activity is detectable in the supernatant of the yeast culture.

```
              (Pro) Leu  Asp  Lys  Arg  Thr  (Tyr)
                              1    2
      5'       CT   TTG  GAT  AAA  AGA  ACG  T
IIIa  3'  CAT  GGA  AAC  CTA  TTT  TCT  TGC  ATA
         (KpnI)                         (AccI)
```

```
              (Pro) Leu  Asp  Lys  Arg  Ile  (Tyr)
                              1    2
      5'       CT   TTG  GAT  AAA  AGA  ATA  T
IIIb  3'  CAT  GGA  AAC  CTA  TTT  TCT  TAT  ATA
         (KpnI)
```

When DNA sequence IIIb is used, the vectors corresponding to cloning vectors 7 and 8 (Table 2) do not contain the AccI cleavage site.

TABLE 1

DNA sequences

```
                              50                           55
I.   5'      C  GAT  GTT  GCT  GTT  TTG  CCA  TTC  TCC
     3'         TA   CAA  CGA  CAA  AAC  GGT  AAG  AGG
            (TaqI)
                                    60                      65
             AAC  AGT  ACT  AAT  AAC  GGT  TTA  TTG  TTC
             TTG  TCA  TGA  TTA  TTG  CCA  AAT  AAC  AAG

70
             ATT  AAT  ACT  ACT  ATT  GCT  AGC  ATT  GCT
             TAA  TTA  TGA  TGA  TAA  CGA  TCG  TAA  CGA 75                     80
             GCT  AAA  GAA  GAA  GGG  GTA  C        3'
             CGA  TTT  CTT  CTT  CCC            5'
                                          (kpnI)

II.  5'  CATGGA           3'
     3'  GTACCTTCGA       5'
           (HindIII)

(Pro) Leu  Asp  Lys  Arg  Leu  Thr  (Tyr)
III. 5'         CT   TTG  GAT  AAA  AGA  CTT  ACG  T        3'
     3'  CAT  GGA  AAC  CTA  TTT  TCT  GAA  TGC  ATA  5'
        (KpnI)                              (AccI)
```

DNA sequence IV

```
Triplet No.
Amino acid
Nucleotide No.                    0    1    2    3    4    5
                                  Met  Thr  Tyr  Thr  Asp  Cys
                         1             10
Cod. strand      5'   CT  AGA ATG  ACG  TAT  ACT  GAC  TGC
Non-cod. strand  3'        T  TAC  TGC  ATA  TGA  CTG  ACG 6    7    8    9    10   11   12   13   14   15
Thr  Glu  Ser  Gly  Gln  Asn  Leu  Cys  Leu  Cys
                         40                  50
ACT  GAA  TCT  GGT  CAG  AAC  CTG  TGC  CTG  TGC
TGA  CTT  AGA  CCA  GTC  TTG  GAC  ACG  GAC  ACG 16   17   18   19   20   21   22   23   24   25
Glu  Gly  Ser  Asn  Val  Cys  Gly  Gln  Gly  Asn
               60             70
GAA  GGA  TCT  AAC  GTT  TGC  GGC  CAG  GGT  AAC
CTT  CCT  AGA  TTG  CAA  ACG  CCG  GTC  CCA  TTG 26   27   28   29   30   31   32   33   34   35
Lys  Cys  Ile  Leu  Gly  Ser  Asp  Gly  Glu  Lys
          90             100            110
AAA  TGC  ATC  CTT  GGA  TCC  GAC  GGT  GAA  AAG
TTT  ACG  TAG  GAA  CCT  AGG  CTA  CCA  CTT  TTC 36   37   38   39   40   41   42   43   44   45
Asn  Gln  Cys  Val  Thr  Gly  Glu  Gly  Thr  Pro
          120            130            140
AAC  CAG  TGC  GTT  ACT  GGC  GAA  GGT  ACC  CCG
TTG  GTC  ACG  CAA  TGA  CCG  CTT  CCA  TGG  GGC 46   47   48   49   50   51   52   53   54   55
Lys  Pro  Gln  Ser  His  Asn  Asp  Gly  Asp  Phe
          150            160            170
AAA  CCG  CAG  TCT  CAT  AAC  GAC  GGC  GAC  TTC
TTT  GGC  GTC  AGA  GTA  TTG  CTG  CCG  CTG  AAG 56   57   58   59   60   61   62   63   64
Glu  Glu  Ile  Pro  Glu  Glu  Tyr  Leu  Gln  Stp
```

TABLE 1-continued

DNA sequences

```
        180                    190                 200
GAA GAG ATC CCT GAG GAA TAC CTT CAG TAA
CTT CTC TAG GGA CTC CTT ATG GAA GTC ATT

210
TAG AGC TCG              3'
ATC TCG AGC AGC T        5'
```

TABLE 2

Cloning vectors

| No. | pUC | |
|---|---|---|
| 1 | 19 | -E . . . (1.75 kb α-Fragment) . . . E- |
| 2 | 18 | -K . . . (α-80-49) . . . T . . . (α-48-8) . . . P- |
| 3 | 19 | -B-K . . . (α-80-49) . . . T . . . (α-48-8) . . . P . . . E- |
| 4 | 8 | -B - - - (Hir31-64)-S-Hc-Hd- |
| 5 | 8 | -B - - - (Hir31-64)-S-N-Hd- |
| 6 | 12 | -B - - - (Hir30-3) - - - A - - - X-A- |
| 7 | 19 | -Hd-B - - - (Hir30-3) - - - A - - - K . . . (α-80-8) . . . P . . . E- |
| 8 | 19 | -Hd-N-S - - - (Hir64-3) - - - A - - - K . . . (α-80-8) . . . P . . . E- |

. . . Mfα sequences
- - - hirudin sequences

Abbreviations for restriction enzymes
A = AccI
B = BamHI
E = EcoRI
Hc = HincII
Hd = HindIII
K = KpnI
N = NcoI
P = PstI
S = SalI
T = TaqI
X = XbaI

We claim:

1. A hirudin derivative with the amino acid sequence

```
 0                                           1
Leu—Thr—Tyr—Thr—Asp—Cys—Thr—Glu—Ser—Gly—
10
Gln—Asn—Leu—Cys—Leu—Cys—Glu—Gly—Ser—Asn—
20
Val—Cys—Gly—Gln—Gly—Asn—Lys—Cys—Ile—Leu—
30
Gly—Ser—Asp—Gly—Glu—Lys—Asn—Gln—Cys—Val—
40
Thr—Gly—Glu—Gly—Thr—Pro—Lys—Pro—Gln—Ser—
50
His—Asn—Asp—Gly—Asp—Phe—Glu—Glu—Ile—Pro—
60
Glu—Glu—Tyr—Leu—Gln.
```

2. DNA coding for the polypeptide having the amino acid sequence as claimed in claim 1.

3. Vectors containing a DNA sequence as claimed in claim 2.

4. A process for the preparation of a polypeptide as claimed in claim 1, which comprises expression of a DNA as claimed in claim 2 in a host cell.

5. The process as claimed in claim 4, wherein the host cell is a yeast cell.

6. A pharmaceutical containing a polypeptide as claimed in claim 1.

* * * * *